US009888860B2

(12) United States Patent
Han et al.

(10) Patent No.: US 9,888,860 B2
(45) Date of Patent: Feb. 13, 2018

(54) METHODS AND SYSTEMS FOR IDENTIFYING AND MAPPING CARDIAC ACTIVATION WAVEFRONTS

(71) Applicant: St. Jude Medical, Cardiology Division, Inc., St. Paul, MN (US)

(72) Inventors: Dongfeng Han, St. Paul, MN (US); Valtino X. Afonso, Oakdale, MN (US); Chin-Ann Yang, Minneapolis, MN (US); Dennis J. Morgan, Crystal, MN (US); Carlo Pappone, Cernusco Lombardone (IT)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 15/252,498

(22) Filed: Aug. 31, 2016

(65) Prior Publication Data
US 2017/0055864 A1    Mar. 2, 2017

Related U.S. Application Data

(60) Provisional application No. 62/213,434, filed on Sep. 2, 2015.

(51) Int. Cl.
*A61B 5/04* (2006.01)
*A61B 5/02* (2006.01)
(Continued)

(52) U.S. Cl.
CPC ...... *A61B 5/04011* (2013.01); *A61B 5/02028* (2013.01); *A61B 5/044* (2013.01);
(Continued)

(58) Field of Classification Search
CPC ............ A61B 5/04011; A61B 5/02028; A61B 5/04012; A61B 5/0422
See application file for complete search history.

(56) References Cited

U.S. PATENT DOCUMENTS

| 5,697,377 A | 12/1997 | Wittkampf |
| 5,983,126 A | 11/1999 | Wittkampf |

(Continued)

FOREIGN PATENT DOCUMENTS

| EP | 1070480 | 1/2001 |
| WO | 2012092016 | 7/2012 |

OTHER PUBLICATIONS

International Search Report and Written Opinion for PCT/US20161049580, dated Nov. 25, 2016.
(Continued)

*Primary Examiner* — Joseph Dietrich
(74) *Attorney, Agent, or Firm* — Wiley Rein LLP

(57) ABSTRACT

A map of cardiac activation wavefronts can be created from a plurality of mesh nodes, each of which is assigned a conduction velocity vector. Directed edges are defined to interconnect the mesh nodes, and weights are assigned to the directed edges, thereby creating a weighted directed conduction velocity graph. A user can select one or more points within the weighted directed conduction velocity graph (which do not necessarily correspond to nodes), and one or more cardiac activation wavefronts passing through these points can be identified using the weighted directed conduction velocity graph. The cardiac activation wavefronts can then be displayed on a graphical representation of the cardiac geometry.

22 Claims, 10 Drawing Sheets

(51) Int. Cl.
*A61B 5/044* (2006.01)
*A61B 5/042* (2006.01)
*A61B 5/0452* (2006.01)
*A61B 5/00* (2006.01)

(52) U.S. Cl.
CPC ........ *A61B 5/04012* (2013.01); *A61B 5/0422* (2013.01); *A61B 5/0452* (2013.01); *A61B 5/7278* (2013.01); *A61B 5/743* (2013.01)

(56) References Cited

U.S. PATENT DOCUMENTS

| | | |
|---|---|---|
| 6,187,032 B1 | 2/2001 | Ohyu et al. |
| 6,301,496 B1 | 10/2001 | Reisfeld |
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,263,397 B2 | 8/2007 | Hauck et al. |
| 7,885,707 B2 | 2/2011 | Hauck |
| 8,768,440 B1 | 7/2014 | Brodnick et al. |
| 2002/0055674 A1 | 5/2002 | Ben-Haim et al. |
| 2013/0006131 A1 | 1/2013 | Narayan et al. |
| 2016/0089048 A1 | 3/2016 | Brodnick et al. |

OTHER PUBLICATIONS

Richter, Ulrike et al., Propagation Pattern Analysis During Atrial Fibrillation Based on Sparse Modeling, IEEE Transactions on Biomedical Engineering, vol. 59, No. 5, May 2012.

Mase, M. et al., Automatic Reconstruction of Activation and Velocity Maps from Electro-Anatomic Data by Radial Basis Functions, 32nd Annual International Conference of the IEEE EMBS, 2608-2611, Aug. 31-Sep. 4, 2010.

Berens, Philipp, CircStat: A MATLAB Toolbox for Circular Statistics, Journal of Statistical Software, vol. 31, Issue 10, 1-21, Sep. 2009.

Barnette, Alan R. et al., Estimation of 3-D Conduction Velocity Vector Fields from Cardiac Mapping Data, IEEE Biomedical Engineering, vol. 47, No. 8, 1027-1035, Aug. 2000.

Bayly, Philip V. et al., Estimation of Conduction Velocity Vector Fields from Epicardial Mapping Data, IEEE Transactions on Biomedical Engineering, vol. 45, No. 5, 563-571, May 1998.

$$\overrightarrow{CV_k} \quad \theta_{k,i} = \hat{\theta}_{i,j}$$
$$\overrightarrow{CV_i}$$

$$\overrightarrow{CV_i} \quad \theta_{i,j}$$
$$\overrightarrow{CV_j}$$

METHODS AND SYSTEMS FOR IDENTIFYING AND MAPPING CARDIAC ACTIVATION WAVEFRONTS

CROSS-REFERENCE TO RELATED APPLICATIONS

This application claims the benefit of U.S. provisional application No. 62/213,434, filed 2 Sep. 2015, which is hereby incorporated by reference as though fully set forth herein.

BACKGROUND

The instant disclosure relates to electrophysiological mapping, such as may be performed in cardiac diagnostic and therapeutic procedures. In particular, the instant disclosure relates to systems, apparatuses, and methods for identifying and mapping cardiac activation wavefronts.

A conduction velocity ("CV") map in an intra-cardiac navigation and mapping system displays the direction and speed of the electrical conduction at a given map point. The CV map can be computed by gathering local activation times ("LAT") of neighboring points, or by other methodologies.

Given a CV map, it can also be of interest in an electrophysiology study to identify different wavefront patterns. Multiple wavefront patterns might occur during cardiac activations, including, for example, collision, focal, re-entry, and rotor. The identification and interpretation of these wavefronts can help analyze mechanistic properties of a broad range of electrophysiological pathologies. To study these wavefront patterns, however, one must first be able to identify them (e.g., as a group of conduction velocity vectors in the CV map associated with the same source).

BRIEF SUMMARY

Disclosed herein is a method of mapping a cardiac activation wavefront, including the steps: receiving a geometry of at least a portion of a cardiac surface, the geometry including a plurality of nodes; receiving electrophysiology data for the portion of the cardiac surface, the electrophysiology data including conduction velocity data; assigning a conduction velocity vector to each node of the plurality of nodes using the conduction velocity data, thereby creating a plurality of conduction velocity vectors; defining a plurality of directed edges connecting the plurality of nodes, thereby creating a directed conduction velocity graph; assigning a weight to each directed edge of the plurality of directed edges in the directed conduction velocity graph, thereby creating a weighted directed conduction velocity graph; and identifying a cardiac activation wavefront using the weighted directed conduction velocity graph.

The step of assigning a conduction velocity vector to each node of the plurality of nodes using the conduction velocity data can include interpolating the conduction velocity data to assign each conduction velocity vector to an associated node of the plurality of nodes.

The step of defining a plurality of directed edges connecting the plurality of nodes can include repeating, a plurality of times: selecting a first node within the plurality of nodes, the first node having assigned thereto a first conduction velocity vector; selecting a second node within the plurality of nodes, the second node having assigned thereto a second conduction velocity vector; defining a first vector connecting the first node to the second node; defining a second vector connecting the second node to the first node; computing a first angle between the first conduction velocity vector and the first vector; computing a second angle between the second conduction velocity vector and the second vector; defining a directed edge from the first node to the second node when the first angle is less than 90 degrees; and defining a directed edge from the second node to the first node when the second angle is less than 90 degrees.

In some embodiments, the step of assigning a weight to each directed edge of the plurality of directed edges in the directed conduction velocity graph can include, for each directed edge, assigning a weight based upon a first conduction velocity vector assigned to a first node of the respective directed edge and a second conduction velocity vector assigned to a second node of the respective directed edge.

In other embodiments, the step of assigning a weight to each directed edge of the plurality of directed edges in the directed conduction velocity graph can include, for each directed edge, assigning a weight based upon a time required to travel between a first node of the respective directed edge and a second node of the respective directed edge.

In still other embodiments, the step of assigning a weight to each directed edge of the plurality of directed edges in the directed conduction velocity graph can include, for each directed edge, assigning a weight based upon a first peak-to-peak voltage at a first node of the respective directed edge and a second peak-to-peak voltage at a second node of the respective directed edge.

In yet further embodiments, the step of assigning a weight to each directed edge of the plurality of directed edges in the directed conduction velocity graph can include, for each directed edge, assigning a weight based upon a first cycle length at a first node of the respective directed edge and a second cycle length at a second node of the respective directed edge.

In still other embodiments, the step of assigning a weight to each directed edge of the plurality of directed edges in the directed conduction velocity graph can include, for each directed edge, assigning a weight based upon a first direction of a first conduction velocity vector assigned to a first node of the respective directed edge and a second direction of a second conduction velocity vector assigned to a second node of the respective directed edge.

In yet further embodiments, the step of assigning a weight to each directed edge of the plurality of directed edges in the directed conduction velocity graph can include, for each directed edge, assigning a weight based upon one or more of conduction velocity consistency, conduction velocity regularity, electrogram morphological similarity, and contact force.

According to aspects of the disclosure, the step of identifying a cardiac activation wavefront using the weighted directed conduction velocity graph can include: identifying a subset of the plurality of nodes, through which the cardiac activation wavefront passes; identifying a source node within the subset of the plurality of nodes; and identifying a path of the cardiac activation wavefront, starting with the source node, through the subset of the plurality of nodes.

In other aspects of the disclosure, the step of identifying a subset of the plurality of nodes can include: selecting a seed node within the plurality of nodes; adding the seed node to the subset of the plurality of nodes; and applying a growing algorithm starting from the seed node to add one or more additional nodes to the subset of the plurality of nodes, wherein the growing algorithm: computes a similarity measurement between a first node within the subset of the plurality of nodes and a second node, adjacent the first node and outside of the subset of the plurality of nodes, and adds the second node to the subset of the plurality of nodes when the similarity measurement satisfies a similarity criterion. The similarity measurement can be based, at least in part, upon a direction of a conduction velocity vector assigned to the first node and a direction of a conduction velocity vector assigned to the second node.

The step of identifying a source node within the subset of the plurality of nodes can include applying a strongly connected components analysis to the subset of the plurality of nodes.

The step of identifying a path of the cardiac activation wavefront, starting with the source node, through the subset of the plurality of nodes can include identifying a lowest-cost path, starting with the source node, through the subset of the plurality of nodes.

It is also contemplated that the method can include: displaying a graphical representation of the geometry; and displaying a graphical representation of the cardiac activation wavefront on the graphical representation of the geometry. The step of displaying a graphical representation of the cardiac activation wavefront on the graphical representation of the geometry can include animating the graphical representation of the cardiac activation wavefront on the graphical representation of the geometry. For example, the graphical representation of the cardiac activation wavefront can be animated over a time duration based upon a mean cardiac cycle length.

In other aspects of the disclosure, the step of identifying a cardiac activation wavefront using the weighted directed conduction velocity graph includes: identifying a first cardiac activation wavefront using the weighted directed conduction velocity graph; and identifying a second cardiac activation wavefront using the weighted directed conduction velocity graph, and wherein the method further includes: displaying a graphical representation of the geometry; displaying a graphical representation of the first cardiac activation wavefront on the graphical representation of the geometry; and displaying a graphical representation of the second cardiac activation wavefront on the graphical representation of the geometry after preset delay time has elapsed following displaying the graphical representation of the first cardiac activation wavefront.

In still other aspects of the disclosure, the step of identifying a cardiac activation wavefront using the weighted directed conduction velocity graph includes: identifying a first cardiac activation wavefront using the weighted directed conduction velocity graph; and identifying a second cardiac activation wavefront using the weighted directed conduction velocity graph, and wherein the method further includes: determining that the first cardiac activation wavefront and the second cardiac activation wavefront should be merged; merging the first cardiac activation wavefront and the second cardiac activation wavefront into a merged cardiac activation wavefront; displaying a graphical representation of the geometry; and displaying a graphical representation of the merged cardiac activation wavefront; on the graphical representation of the geometry.

In further aspects of the disclosure, the step of identifying a cardiac activation wavefront using the weighted directed conduction velocity graph includes: identifying a source of the cardiac activation wavefront using the weighted directed conduction velocity graph; and identifying a path of the cardiac activation wavefront through the weighted directed conduction velocity graph.

Also disclosed herein is a method of mapping cardiac activation wavefronts, including: establishing a mesh including a plurality of mesh nodes; assigning each mesh node of the plurality of mesh nodes a conduction velocity vector; defining a plurality of weighted directed edges interconnecting the plurality of mesh nodes, thereby creating a weighted directed conduction velocity graph; identifying at least one cardiac activation wavefront using the weighted directed conduction velocity graph; and displaying the identified at least one cardiac activation wavefront on a graphical representation of a cardiac geometry.

The instant disclosure also relates to a system for mapping cardiac activation wavefronts, including: a cardiac activation wavefront identification processor configured: to receive as input a mesh comprising a plurality of mesh nodes and electrophysiology data comprising conduction velocity data; to assign a conduction velocity vector to each mesh node of the plurality of mesh nodes using the conduction velocity data; to define a plurality of weighted directed edges interconnecting the plurality of mesh nodes, thereby creating a weighted directed conduction velocity graph; and to identify at least one cardiac activation wavefront using the weighted directed conduction velocity graph; and a mapping processor configured to display the identified at least one cardiac activation wavefront on a graphical representation of a cardiac geometry.

The foregoing and other aspects, features, details, utilities, and advantages of the present invention will be apparent from reading the following description and claims, and from reviewing the accompanying drawings.

DETAILED DESCRIPTION

The present disclosure provides methods, apparatuses, and systems for the creation of electrophysiology maps (e.g., electrocardiographic maps) including cardiac activation wavefronts.

Figure 1:
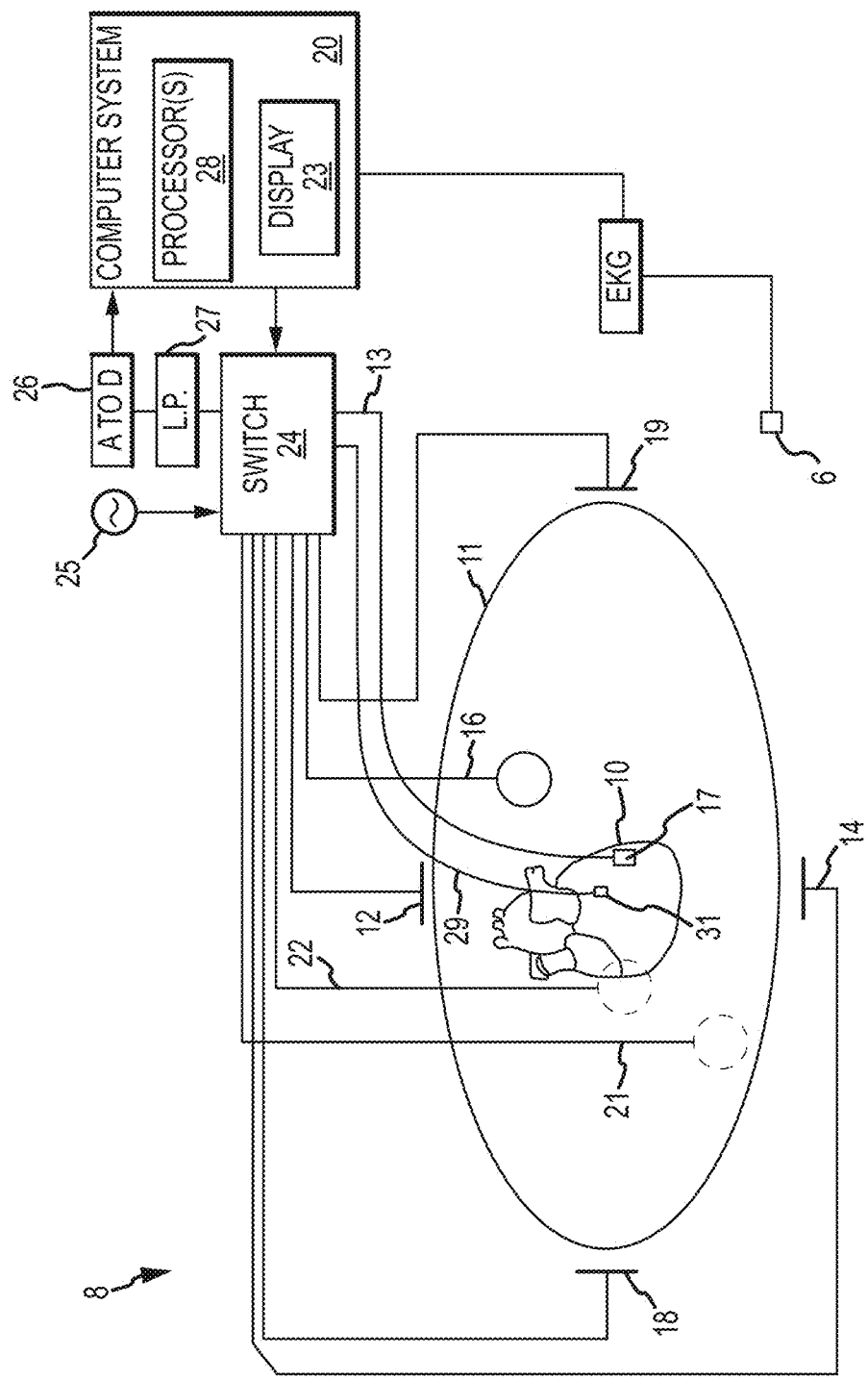
FIG. 1 is a schematic of an electrophysiology system, such as may be used in an electrophysiology study.

FIG. 1 shows a schematic diagram of an electrophysiology system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data, including, but not limited to, local activation time ("LAT"), at a plurality of points along a cardiac surface and store the measured data in association with location information for each measurement point at which the electrophysiology data was measured, for example to create a diagnostic data map of the patient's heart 10.

As one of ordinary skill in the art will recognize, and as will be further described below, system 8 can determine the location, and in some aspects the orientation, of objects, typically within a three-dimensional space, and express those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body or on an external frame.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only one lead 6 and its connection to computer system 20 is illustrated in FIG. 1.

A representative catheter 13 having at least one electrode 17 (e.g., a distal electrode) is also depicted in schematic fashion in FIG. 1. This representative catheter electrode 17 can be referred to as a "measurement electrode" or a "roving electrode." Typically, multiple electrodes on catheter 13, or on multiple such catheters, will be used. In one embodiment, for example, system 8 may utilize sixty-four electrodes on twelve catheters disposed within the heart and/or vasculature of the patient.

In other embodiments, system 8 may utilize a single catheter that includes multiple (e.g., eight) splines, each of which in turn includes multiple (e.g., eight) electrodes. Of course, these embodiments are merely exemplary, and any number of electrodes and catheters may be used. Indeed, in some embodiments, a high density mapping catheter, such as the EnSite™ Array™ non-contact mapping catheter of St. Jude Medical, Inc., can be utilized.

Figure 2:
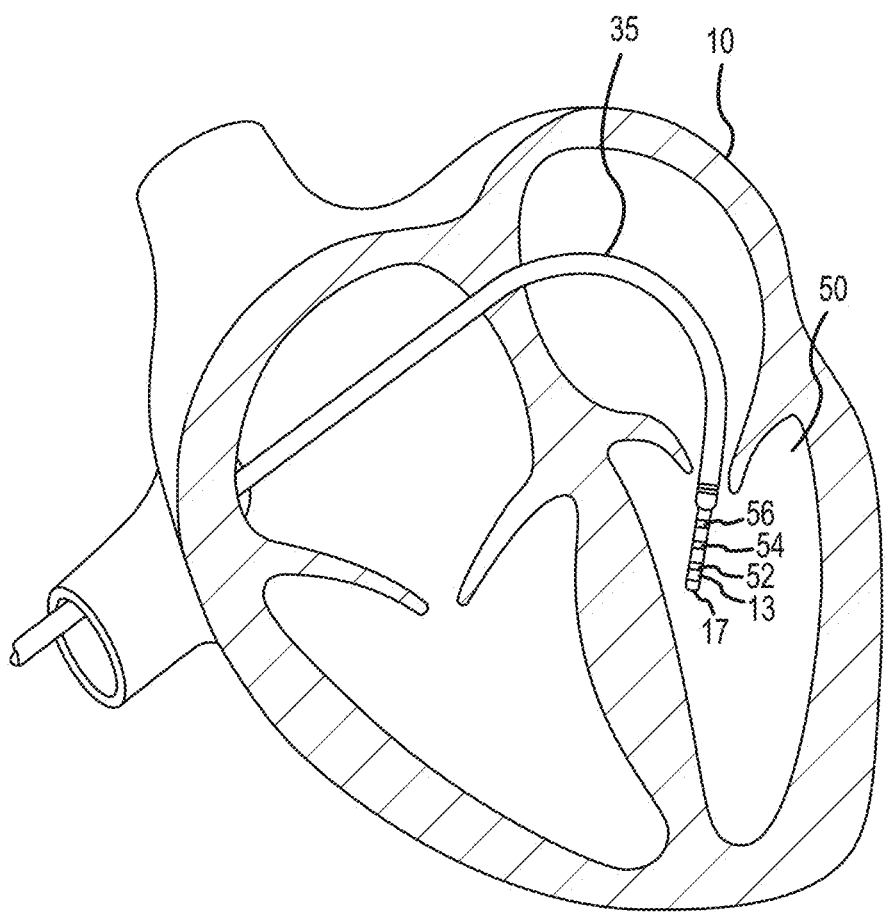
FIG. 2 depicts an exemplary multi-electrode catheter used in an electrophysiology study.

Likewise, it should be understood that catheter 13 (or multiple such catheters) are typically introduced into the heart and/or vasculature of the patient via one or more introducers and using familiar procedures. For purposes of this disclosure, a segment of an exemplary multi-electrode catheter 13 is shown in FIG. 2. In FIG. 2, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart 10 in any other suitable manner.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8.

Similarly, each of electrodes 17, 52, 54, and 56 can be used to gather electrophysiological data from the cardiac surface. The ordinarily skilled artisan will be familiar with various modalities for the acquisition and processing of electrophysiology data points (including, for example, both contact and non-contact electrophysiological mapping), such that further discussion thereof is not necessary to the understanding of the conduction velocity mapping techniques disclosed herein. Likewise, various techniques familiar in the art can be used to generate a graphical representation from the plurality of electrophysiology data points. Insofar as the ordinarily skilled artisan will appreciate how to create electrophysiology maps from electrophysiology data points, the aspects thereof will only be described herein to the extent necessary to understand the maps disclosed herein.

Returning now to FIG. 1, in some embodiments, a fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20, for example, may comprise a conventional general-purpose computer, a special-purpose computer, a distributed computer, or any other type of computer. The computer 20 may comprise one or more processors 28, such as a single central processing unit (CPU), or a plurality of processing units, commonly referred to as a parallel processing environment, which may execute instructions to practice the various aspects disclosed herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any other number of electrodes) could be positioned in any other effective arrangement for driving a current to or sensing a current from an electrode in the heart. For example, multiple electrodes could be placed on the back, sides, and/or belly of patient 11. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart 10 may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the roving electrodes 17, 52, 54, 56 within heart 10.

The measured voltages may be used by system 8 to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

In one representative embodiment, the system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ cardiac mapping and visualization system of St. Jude Medical, Inc., which generates electrical fields as described above, or another localization system that relies upon electrical fields. Other localization systems, however, may be used in connection with the present teachings, including for example, systems that utilize magnetic fields instead of or in addition to electrical fields for localization. Examples of such systems include, without limitation, the CARTO navigation and location system of Biosense Webster, Inc., the AURORA® system of Northern Digital Inc., Sterotaxis' NIOBE® Magnetic Navigation System, as well as Medi-Guide™ Technology and the EnSite™ Precision™ system, both from St. Jude Medical, Inc.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

U.S. provisional application No. 62/063,987, filed 15 Oct. 2014 and hereby incorporated by reference as though fully set forth herein, discloses methods, apparatuses, and systems for the creation of electrophysiology maps that provide information regarding the local conduction velocity of a cardiac activation wavefront. In such a map (referred to herein as a "CV map,"), it is desirable to be able to identify different wavefront patterns (e.g., collision, focal, re-entry, rotor). Thus, it is desirable to identify wavefronts, as a group of conduction velocity vectors, associated with a common source.

Figure 3:
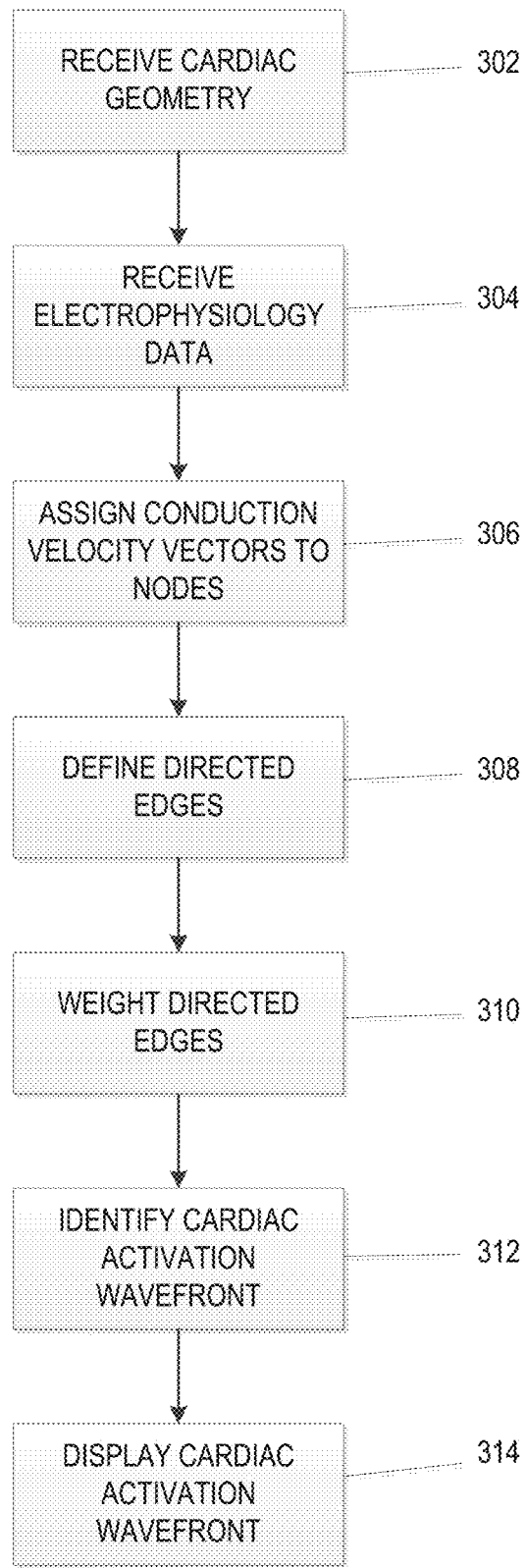
FIG. 3 is a flowchart of representative steps that can be followed to map a cardiac activation wavefront according to an embodiment of the disclosure.

One basic methodology of mapping a cardiac activation wavefront using conduction velocity vector information will be explained herein with reference to the flowchart of representative steps presented as FIG. 3. In some embodiments, for example, the flowchart may represent several exemplary steps that can be carried out by the computer 20 of FIG. 1 (e.g., by one or more processors 28) to identify and map a cardiac activation wavefront as described herein. It should be understood that the representative steps described below can be either hardware- or software-implemented. For the sake of explanation, the term "signal processor" is used herein to describe both hardware- and software-based implementations of the teachings herein.

Figure 4A:
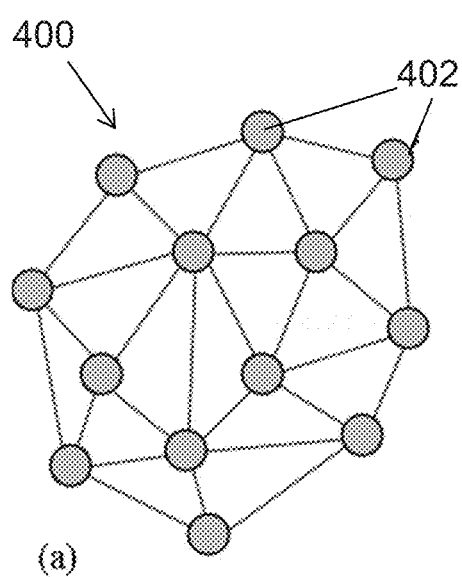
FIG. 4a depicts a representative mesh.

A cardiac geometry (that is, a geometry of at least a portion of a cardiac surface) is received in block 302. As those of ordinary skill in the art will appreciate, the cardiac geometry is defined by a plurality of location points, also referred to herein as "nodes." These nodes can be interconnected by edges; together, the collection of nodes and edges form a mesh that represents the cardiac surface. A representative mesh 400, including a plurality of nodes 402, is illustrated in FIG. 4a.

In some embodiments, the cardiac geometry is acquired using localization system 8. For example, the OneModel™ and/or OneMap™ tools, which are part of St. Jude Medical's EnSite™ Velocity™ cardiac mapping system, can be used to create the cardiac geometry. It is also contemplated, however, that the cardiac geometry can be acquired using other modalities, including, without limitation, MRI, CT, and ultrasound mapping. Further, insofar as the generation and acquisition of a cardiac geometry will be familiar to those of ordinary skill in the art, such that further explanation thereof is not necessary to the understanding of the cardiac activation wavefront mapping techniques disclosed herein.

According to aspects of the instant disclosure, the relative spacing of nodes 402 within mesh 400 can be substantially uniform. For example, nodes 402 can be positioned at a user selectable uniform spacing, such as about 1 mm.

Electrophysiology ("EP") data for the portion of the cardiac surface represented by the cardiac geometry is received in step 304. EP data can be collected, for example, using a multi-electrode catheter 13 as described above. As will be familiar to the person of ordinary skill in the art, and as described above, the EP data describes the electrophysiological activity occurring on the cardiac surface and can include, without limitation, conduction velocity data, local activation time ("LAT") data, voltage data (e.g., peak-to-peak voltage data), fractionation data, and cycle length data.

As described above, the ordinarily skilled artisan will be familiar with EP mapping, such that the aspects thereof will only be described herein to the extent necessary to understand the maps disclosed herein. For purposes of illustration only, therefore, aspects of the cardiac activation wavefront mapping techniques disclosed herein will be described in connection with conduction velocity data, with the understanding that it is within the capability of one of ordinary skill in the art to extend these teachings to other EP data.

Figure 4B:
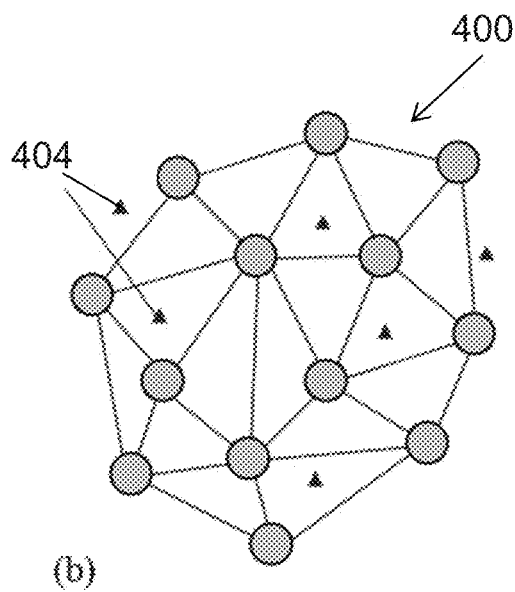
FIG. 4b depicts the representative mesh of FIG. 4a with EP data points.

In some embodiments, the activation wavefront mapping techniques disclosed herein are applied to a conduction velocity map, for example as disclosed in U.S. provisional application No. 62/063,987. In other embodiments, however, the EP data (e.g., the received conduction velocity data) may not map directly to the mesh. That is, the points 404 at which the EP data was measured and/or computed (often referred to as "EP data points" or "map points") may not coincide with the nodes 402 of the cardiac geometry 400. FIG. 4b illustrates this situation.

Figure 4C:
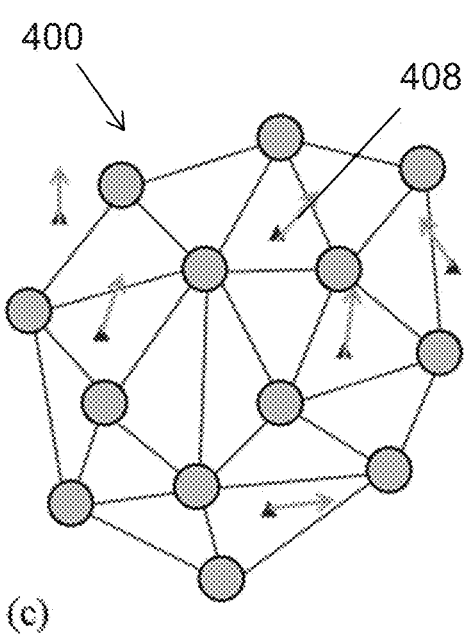
FIG. 4c depicts the representative mesh of FIG. 4a with conduction velocity vectors at EP data points.
Figure 4D:
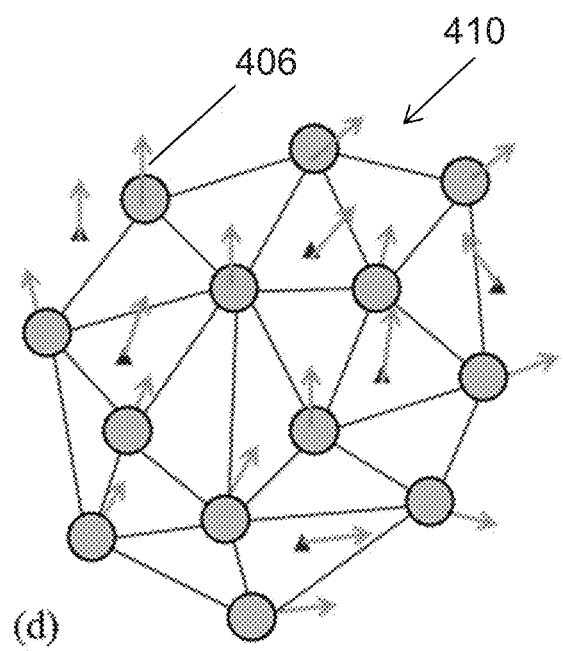
FIG. 4d depicts the assignment of conduction velocity vectors to the nodes of the representative mesh shown in FIG. 4a, referred to herein as a conduction velocity mesh.

As the person of ordinary skill in the art will appreciate from the instant disclosure, it is beneficial in this circumstance to assign EP data to nodes 402 (block 306) using EP data measured at points 404. FIGS. 4c and 4d illustrate one suitable method of assigning conduction velocity vectors 406 to nodes 402 by interpolating conduction velocity data 408 measured at points 404, for example by using a Gaussian kernel.

The output of block 306 is referred to herein as a "conduction velocity mesh" (i.e., a collection of nodes 402 including conduction velocity vectors 406). FIG. 4d illustrates a representative conduction velocity mesh 410 generated by assigning data interpolated from conduction velocity data 408 to nodes 402.

It is contemplated that certain EP data may be excluded when assigning EP data to nodes 402. For example, U.S. provisional application No. 62/063,987 discloses a "consistency index" that measures the degree of consistency in the direction of the conduction velocity vector constituents for a given EP data point over time. A high conduction velocity consistency index can be associated with a high degree of directional consistency, while a lower conduction velocity consistency index can be associated with a low degree of directional consistency (that is, a high degree of randomness in the direction of the conduction velocity vector constituents). According to aspects of the instant disclosure, only conduction velocity data from points 404 exhibiting a suitably high consistency index (e.g., having a consistency index exceeding a preset consistency index threshold, which may be user determined) will be included when assigning conduction velocity vectors to nodes 402.

Likewise, it is contemplated that EP data can be excluded based on other metrics, such has low voltage or high fractionation.

Figure 5:
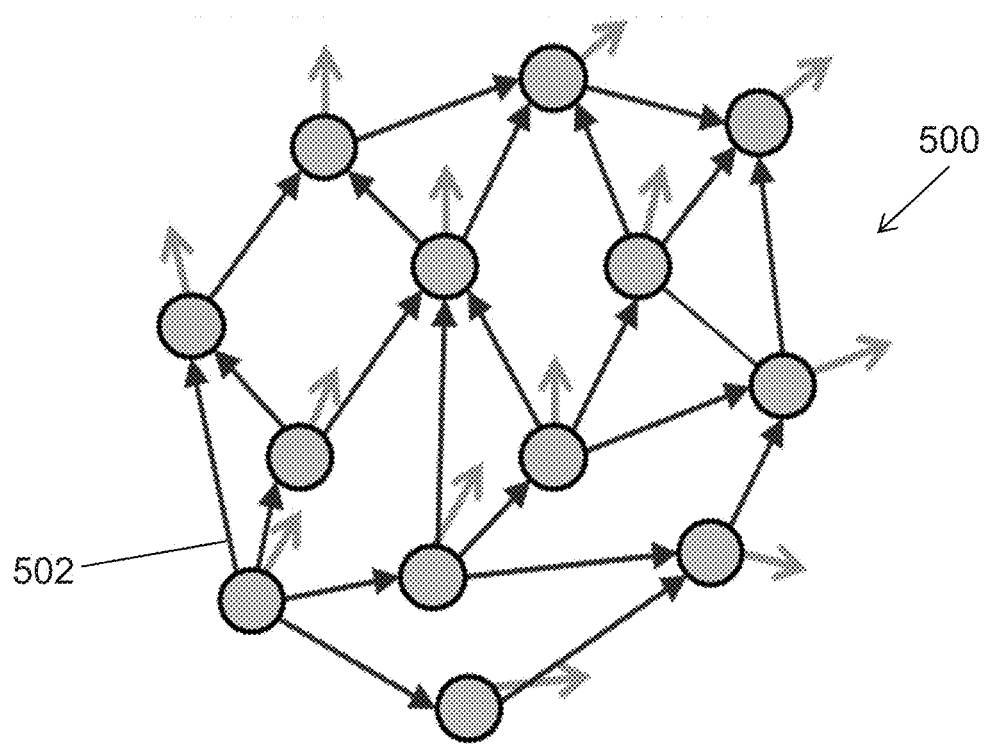
FIG. 5 depicts a representative directed conduction velocity graph.

In block 308, nodes 402 are interconnected by a plurality of directed edges. The result of block 308 is referred to herein as a "directed conduction velocity graph." A representative directed conduction velocity graph 500, corresponding to the conduction velocity mesh 410 shown in FIG. 4d, is illustrated in FIG. 5.

One suitable approach to defining the plurality of directed edges 502 interconnecting nodes 402 will now be described with reference to FIG. 6, which illustrates four possible directed edge scenarios for any pair of nodes i, j having assigned thereto respective conduction velocity vectors $\vec{CV}_I$ and $\vec{CV}_J$. A vector $\vec{D}_{IJ}$ is defined that connects node i to node j, and a vector $\vec{D}_{JI}$ is defined that connects node j to node i. $\vec{CV}_I$ and $\vec{D}_{IJ}$ form an angle $\Theta_{di}$. Likewise, $\vec{CV}_J$ and $\vec{D}_{JI}$ form an angle $\Theta_{dj}$.

Figure 6:
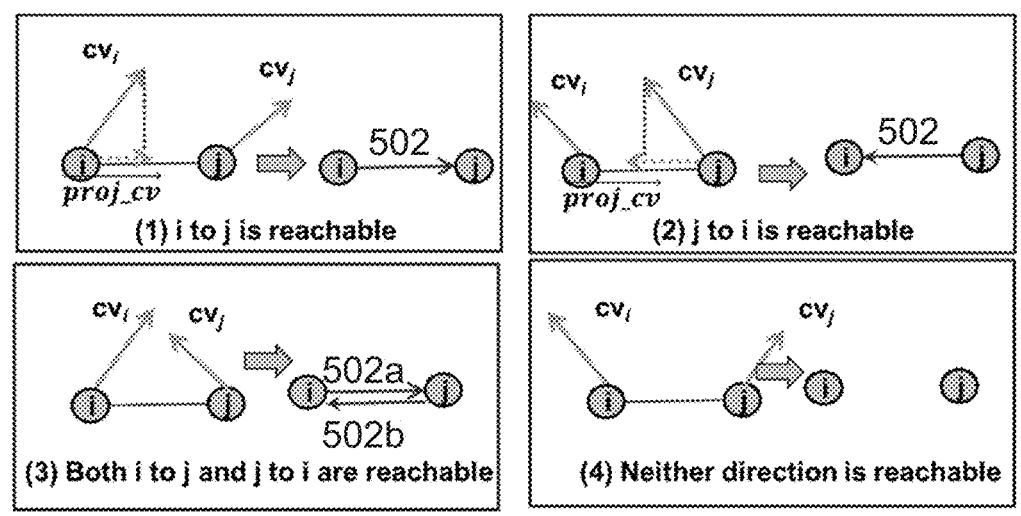
FIG. 6 illustrates various scenarios in the definition of directed edges connecting the nodes of a conduction velocity mesh.

In a first scenario, shown in the upper-left quadrant of FIG. 6, $\Theta_{di}$ is less than 90 degrees and $\Theta_{dj}$ is greater than or equal to 90 degrees. In this scenario, node j is reachable from node i, but not vice versa. Accordingly, a directed edge 502 is defined from node i to node j.

In a second scenario, shown in the upper-right quadrant of FIG. 6, $\Theta_{di}$ is greater than or equal to 90 degrees and $\Theta_{dj}$ is less than 90 degrees. In this scenario, node i is reachable from node j, but not vice versa. Accordingly, a directed edge 502 is defined from node j to node i.

In a third scenario, shown in the lower-left quadrant of FIG. 6, $\Theta_{di}$ and $\Theta_{dj}$ are both less than 90 degrees. In this scenario, each of nodes i and j is reachable from the other. Accordingly, two directed edges, 502a and 502b, are defined from node i to node j and from node j to node i, respectively.

In a fourth scenario, shown in the lower-right quadrant of FIG. 6, both $\Theta_{di}$ and $\Theta_{dj}$ are greater than or equal to 90 degrees. In this scenario, neither node i or j is reachable from the other. Accordingly, no directed edges are defined between nodes i and j.

In block 310, a weight (or cost) is assigned to each directed edge 502. As discussed in further detail below, the weight assigned to a directed edge 502 is a measure of the likelihood that the conduction velocity vectors $\vec{CV}_I$ and $\vec{CV_j}$ at nodes i and j connected by the directed edge 502 result from the same cardiac activation wavefront. That is, the lower the weight, the more likely that $\vec{CV_I}$ and $\vec{CV_J}$ result from the same cardiac activation wavefront. The result of block 310 is referred to herein as a "weighted directed conduction velocity graph."

A weight function W for a directed edge connecting a pair of nodes i, j can be defined using various metrics. Several suitable weight functions W will be described in the following paragraphs. It should be understood that the exemplary weight functions W described hereinafter can be applied both individually and in various combinations. In other words, although the representative weight functions described hereinafter are presented as being functions of only a single metric, it is within the spirit and scope of the instant disclosure to define a weight function as a function of multiple metrics described herein (e.g., a weight function that is both conduction velocity- and time-based).

Conduction Velocity Based Weight Function $W_{CV}(i, j)$. According to an aspect of the instant disclosure, the weight function W is based upon the similarity between the conduction velocity vectors $\vec{CV_I}$ and $\vec{CV_J}$ assigned to nodes i and j, respectively. The angle between these two can be computed according to the formula $$\Theta_{i,j} = \cos^{-1}\left(\frac{\vec{CV_I} \cdot \vec{CV_J}}{|\vec{CV_I}||\vec{CV_J}|}\right),$$

and the difference in magnitude can be computed according to the formula $d_{i,j}=||\vec{CV_I}|-|\vec{CV_J}||$. The weight function W can be a function of both $\Theta_{i,j}$ and $d_{i,j}$, for example $W_{CV}(i, j)=w_1*\Theta_{i,j}+w_2*d_{i,j}$, where $w_1$ and $w_2$ are weighting factors associated with the angle between $\vec{CV_I}$ and $\vec{CV_J}$ and the difference in magnitude between $\vec{CV_I}$ and $\vec{CV_J}$, respectively. According to this representative formula, a directed edge 502 will have a smaller weight if its nodes i and j have similar conduction velocity vectors (reflecting that similar conduction velocity vectors likely result from the same cardiac activation wavefront).

Time-Based Weight Function $W_t(i, j)$. According to another aspect of the instant disclosure, the weight function W is based upon a time required to travel between the two nodes i and j along a directed edge therebetween. This, in turn, can be computed by dividing the distance between nodes i and j by the velocity along the directed edge connecting nodes i and j. For example, if the directed edge runs from node i to node j, then $$W_t(i, j) = \frac{\|\vec{D_{IJ}}\|}{\|\vec{CV_I}\cos\Theta_{di}\|}(\vec{D_{ij}}, \vec{CV_I},$$

and $\Theta_{di}$ are defined above). According to this representative formula, the weight of a directed edge 502 will be directly proportional to the time it takes for a wavefront to propagate along that directed edge.

Voltage-Based Weight Function $W_V(i, j)$. In yet another aspect of the instant disclosure, the weight function W is based upon the similarity between the voltages (e.g., peak-to-peak voltages) $V_i$ and $V_j$ at nodes i and j, respectively. For example, $W_V(i,j)=|V_i-V_j|$. According to this representative formula, a directed edge 502 will have a smaller weight if its nodes i and j have similar peak-to-peak voltages (reflecting that similar peak-to-peak voltages often result from the same cardiac activation wavefront).

Cycle Length-Based Weight Function $W_{CL}(i,j)$. In still another aspect of the instant disclosure, the weight function W is based upon the similarity between the cycle lengths $CL_i$ and $CL_j$ at nodes i and j, respectively. For example, $W_{CL}(i, j)=|CL_i-CL_j|$. According to this formula, a directed edge 502 will have a smaller weight if its nodes i and j have similar cycle lengths (reflecting that similar cycle lengths often result from the same cardiac activation wavefront).

Other Suitable Metrics. Other suitable metrics that can be considered in a weight function include, without limitation, conduction velocity consistency, conduction velocity regularity, electrogram morphological similarity, contact force, or combinations thereof. The ordinarily skilled artisan will appreciate how to develop a weight function using these various metrics (e.g., in a manner that computes a lower weight on a directed edge that interconnects two nodes likely experiencing the same cardiac activation wavefront).

Shape-Dependent Weight Functions. The conduction velocity-, time-, voltage-, and cycle length-based weight functions described above generally assume a constant model for the cardiac activation wavefront. This model, while appropriate for a planar wavefront, does not hold true for other wavefront patterns (e.g., rotational wavefronts).

Thus, in some embodiments, different weight functions can be used for different wavefront patterns, such that the weight function is shape-dependent. For purposes of illustration, shape-dependent weight functions will be described with reference to conduction velocity vector orientations. It should be understood, however, that shape-dependent weight functions can also be developed for any of the other metrics discussed herein (e.g., conduction velocity magnitude, time, voltage, cycle length, conduction velocity consistency, conduction velocity regularity, electrogram morphological consistency, contact force, and the like).

Figure 7A:
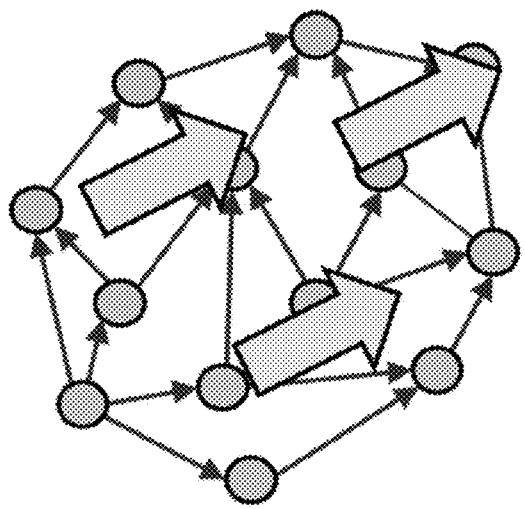
FIG. 7a schematically illustrates a planar cardiac activation wavefront.

A conduction velocity vector orientation-based weight function is a function of $\Theta_{i,j}$ (defined above). For a planar wave, such as shown schematically in FIG. 7a, smaller angles $\Theta_{i,j}$ reflect greater similarity between the orientations of the respective conduction velocity vectors assigned to nodes i and j and should therefore yield a smaller weight. Thus, a suitable conduction velocity vector orientation-based weight function for a planar wave can be defined as $W_{CV}(i, j)=\Theta_{i,j}$.

Figure 7B:
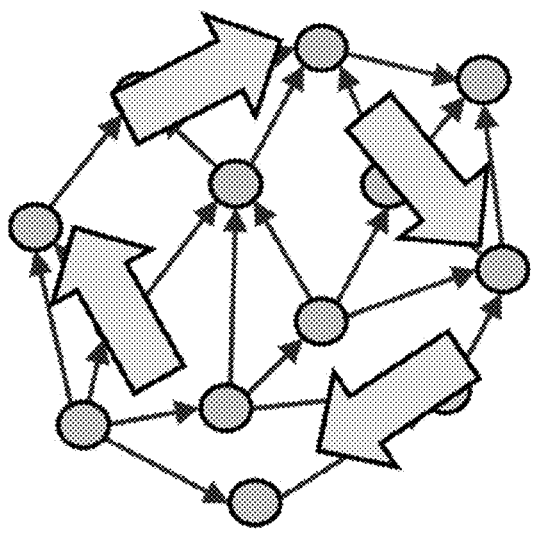
FIG. 7b schematically illustrates a rotary cardiac activation wavefront.

For a rotational wave such as shown schematically in FIG. 7b, on the other hand, there can be considerable variation in the orientations of the conduction velocity vector assigned to the nodes of a directed edge even within the same cardiac activation wavefront. The shape-dependent weight function described above for a planar wave would, therefore, give a "false negative" if applied to a rotational wave.

Figure 7C:
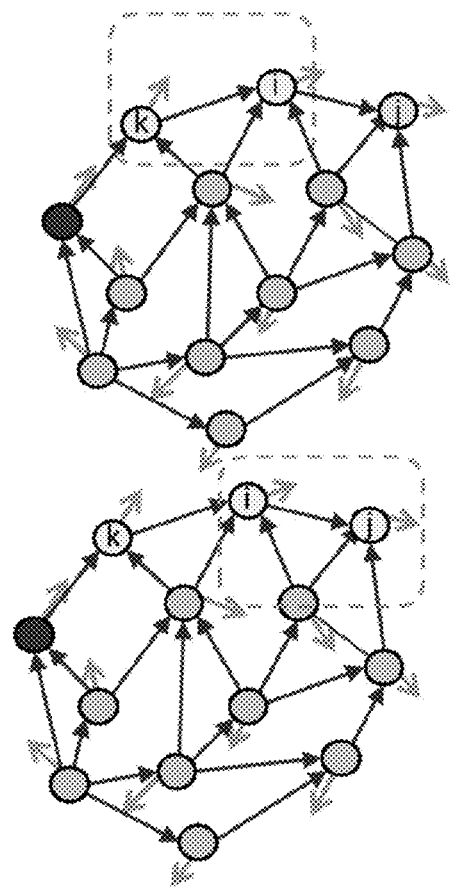
FIG. 7c illustrates a shape-dependent weight functions for a rotary cardiac activation wavefront.

A suitable weight function for a rotational wave, therefore, can be a comparison of two angles between three conduction velocity vectors. As shown in FIG. 7c, three adjacent nodes i, j, and k have assigned thereto respective conduction velocity vectors $\vec{CV_I}$, $\vec{CV_J}$, and $\vec{CV_k}$. $\vec{CV_I}$ and $\vec{CV_J}$ form an angle $\Theta_{i,j}$, while $\vec{CV_I}$ and $\vec{CV_k}$ form an angle $\Theta_{k,i}$.

For a rotational wave, one can expect that the angle with which the wavefront enters a node (e.g., node i) will be similar to the angle with which the wavefront exits that node. Smaller weights should therefore be assigned when $\Theta_{i,j} \sim \Theta_{k,i}$. One suitable shape-dependent weight function for a rotational wave is, accordingly, $W_{CV}(i, j)=\Theta_{k,i}-\Theta_{i,j}$.

Other weight functions for other wave shapes (e.g., focal, collision) and/or weight functions using additional and/or different metrics (e.g., conduction velocity magnitude, peak-to-peak voltage, and the like) are also contemplated.

Figure 8:
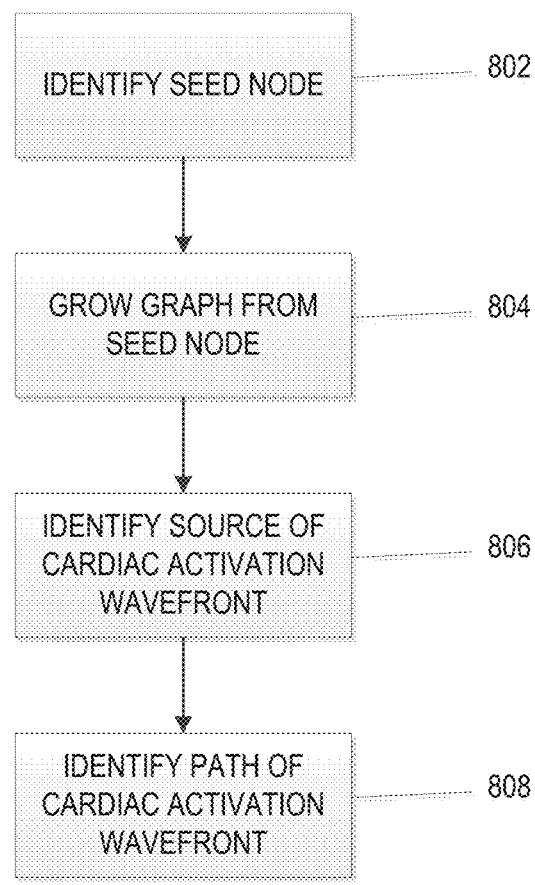
FIG. 8 is a flowchart of representative steps that can be followed to identify a cardiac activation wavefront in a weighted directed conduction velocity graph.

One or more cardiac activation wavefronts are identified using the weighted directed conduction velocity graph in block 312. Further detail of representative steps that can be included in block 312 are shown in the flowchart 800 of FIG. 8.

Figure 9:
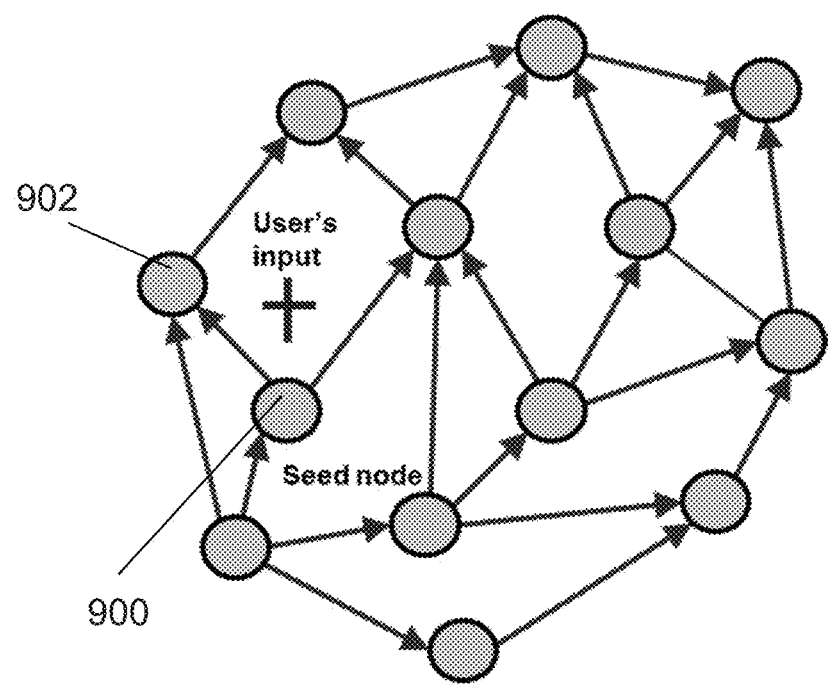
FIG. 9 depicts the identification of a seed node within a weighted directed conduction velocity graph.

In block 802, a seed node is selected, for example by allowing the user to point-and-click on a graphical representation of the weighted directed conduction velocity graph. As shown in FIG. 9, in the event that the user does not precisely select a node, system 8 can interpret the user's input to be a selection of the nearest node as the seed node 900.

Advantageously, the user's selection of a seed node in block 802 can be arbitrary relative to both the weighted directed conduction velocity graph and the cardiac activation wavefront to be identified and/or mapped. That is, not only is the user not required to precisely select a node within the weighted directed conduction velocity graph, the user is also not required to attempt to identify the starting point of a cardiac activation wavefront. Instead, the methods described herein are applied to the arbitrarily-selected seed node 900 to identify the starting point of the cardiac activation wavefront that passes through seed node 900.

According to additional aspects of the disclosure, seed node 900 can be automatically determined, such as by system 8, instead of by user selection. For example, as described above, nodes 402 can have EP data assigned thereto (e.g., conduction velocity, cycle length, or the like). This EP data can be used by system 8 as a criterion to identify seed node 900 (e.g., node 402 with the highest conduction velocity, shortest cycle length, or the like).

Seed node 900 is then "grown," via application of a growing algorithm, to include a subset of the plurality of nodes, through which the same cardiac activation wavefront passes (block 804). The growing algorithm computes a similarity measurement SM(i, j) between adjacent nodes i and j (e.g., between seed node 900 and adjacent node 902 in FIG. 9), compares the similarity measurement to a similarity criterion (e.g., a similarity threshold), and adds the adjacent node 902 to the subset of the plurality of nodes if the similarity measurement satisfies the similarity criterion (e.g., it exceeds the similarity threshold).

One suitable similarity criterion is based on the angle formed by the conduction velocity vectors of adjacent nodes. If the angle $\Theta_{i,j}$ formed by the conduction velocity vectors $\overrightarrow{CV_I}$ and $\overrightarrow{CV_J}$ of adjacent nodes i and j is below a threshold angle α, the adjacent node j is added to the subset. If, on the other hand, the angle exceeds the threshold angle α, then the adjacent node j is not added to the subset.

Figure 10A:
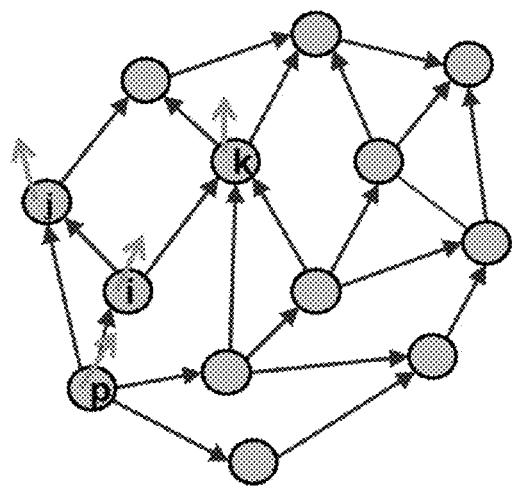
FIGS. 10a-10d illustrate the growth of the seed node identified in FIG. 9 into a subset of nodes, through which a cardiac activation wavefront passes.
Figure 10B:
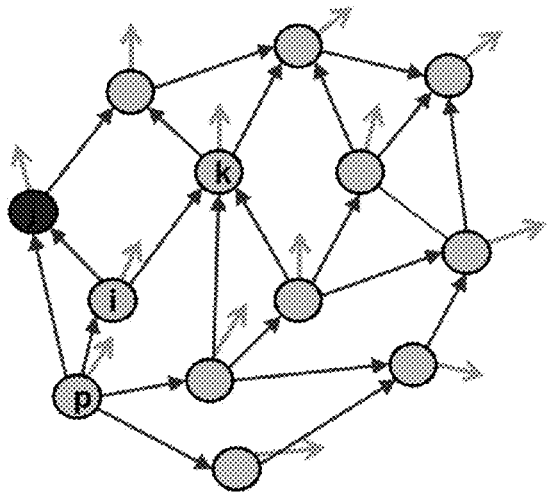
Figure 10C:
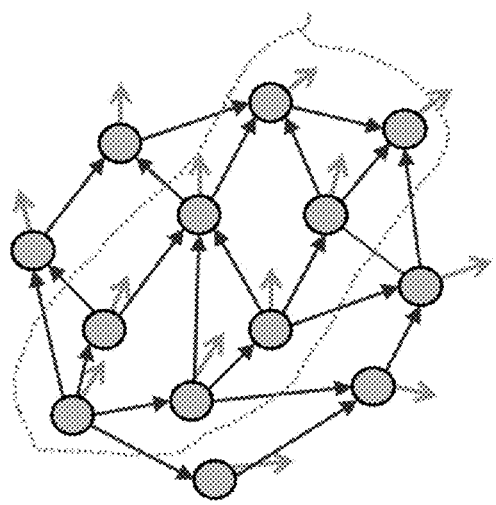
Figure 10D:
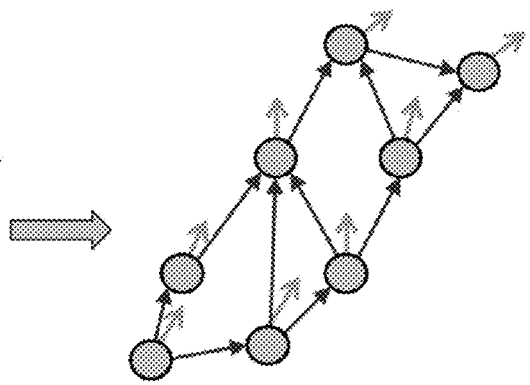

This is further illustrated in FIGS. 10a-10d. FIG. 10a shows a seed node i and three adjacent nodes labeled p, j, and k. As the person of ordinary skill in the art will appreciate from the foregoing disclosure, the conduction velocity vectors assigned thereto are denoted $\overrightarrow{CV_I}$, $\overrightarrow{CV_p}$, $\overrightarrow{CV_J}$, and $\overrightarrow{CV_k}$, respectively. Similarly, the angle between $\overrightarrow{CV_I}$ and $\overrightarrow{CV_p}$ is denoted $\Theta_{p,i}$, the angle between $\overrightarrow{CV_I}$ and $\overrightarrow{CV_J}$ is denoted $\Theta_{i,j}$, and the angle between $\overrightarrow{CV_I}$ and $\overrightarrow{CV_k}$ is denoted as $\Theta_{i,k}$. Each of $\Theta_{p,i}$, $\Theta_{i,j}$, and $\Theta_{i,k}$ is compared to a threshold angle α. As shown in FIG. 10b, for each angle less than α (e.g., $\Theta_{p,i}$ and $\Theta_{i,k}$), the respective adjacent nodes (e.g., p and k) are added to the subset of nodes, through which the cardiac activation wavefront passes. Node j is not added to the subset of nodes, through which the cardiac activation wavefront passes, because $\Theta_{i,j} > \alpha$. This process can repeat iteratively until all nodes have been checked against their adjacent nodes, resulting in the final subset of nodes, through which the cardiac activation wavefront passes, shown in FIGS. 10c (shaded and circled) and 10d (extracted from the surrounding excluded nodes).

Just as different weight functions can be utilized for different wavefront shapes as described above, so too can different similarity measurements be employed without departing from the scope of the instant disclosure. For example, in some embodiments, the similarity measurement SM(i, j) is identical to $W_{CV}(i, j)$ (i.e., the conduction velocity-based weight of the directed edge connecting nodes i and j).

Likewise, the similarity measurement can be a function of multiple metrics. For example, SM(i,j) can be defined as a function of both the conduction velocity-based weight and the cycle length-based weight of the directed edge connecting nodes i and j: $\Theta_1 W_{CV}(i, j) + \Theta_2 W_{CL}(i, j)$.

In still other embodiments, the growth process is repeated using a second similarity measurement independent of the first similarity measurement.

Once the subset of nodes, through which the cardiac activation wavefront passes, is identified, the source node (i.e., the node corresponding to the origin of the cardiac activation wavefront) is determined in block 806. According to aspects of the disclosure, the *Strongly Connected Components Analysis* (see Sharir, *A strong connectivity algorithm and its applications to data flow analysis*, Computers and Mathematics with Applications 7(1):67-72 (1981); Cormen, *Introduction to algorithms* (2009), both of which are hereby incorporated by reference as though fully set forth herein)) is applied to identify the source node.

In block 808, the path of the cardiac activation wavefront through the subset of nodes and starting with the source node is identified. In embodiments disclosed herein, the path of the cardiac activation wavefront is determined by seeking the lowest cost path through the subset of nodes.

Figure 11:
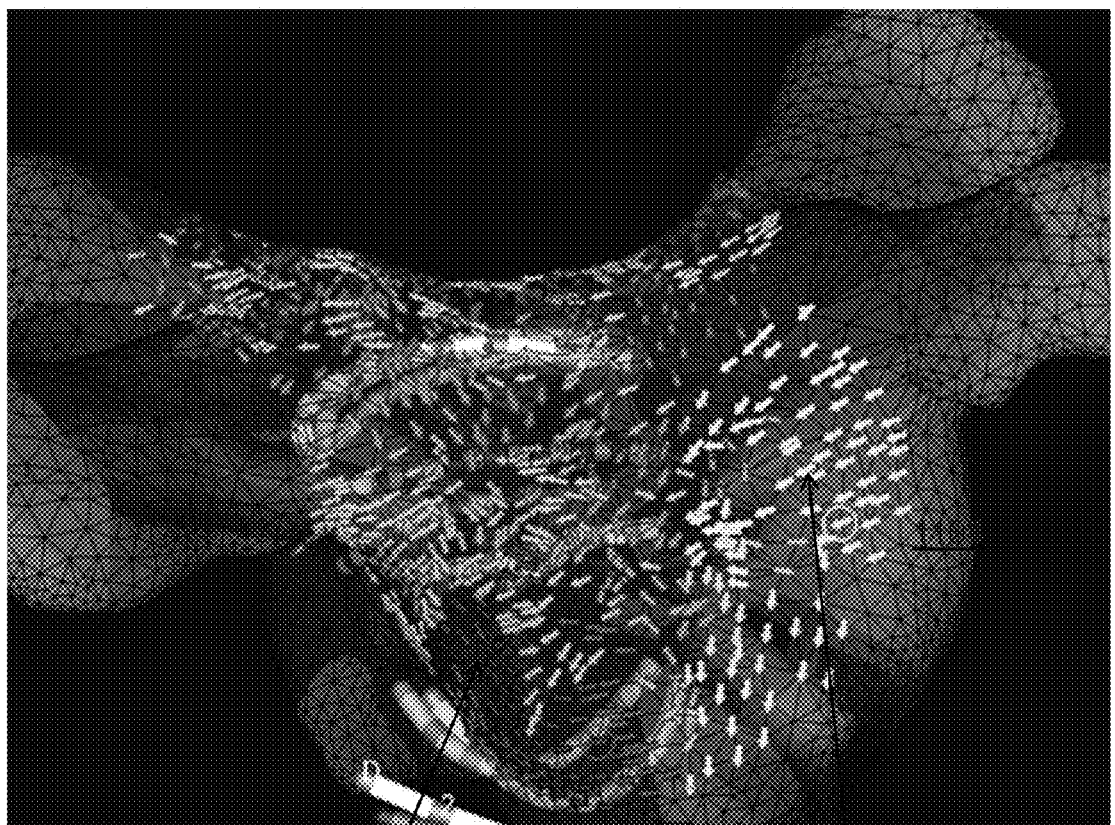
FIG. 11 depicts an approach to displaying cardiac activation wavefronts on a conduction velocity map according to aspects of the instant disclosure.

Returning now to FIG. 3, in block 314, the cardiac activation wavefront can be displayed, such as on a graphical representation of the cardiac geometry on display 23. One representative approach to displaying cardiac activation wavefronts is shown in FIG. 11. As shown in FIG. 11, two identified cardiac activation wavefronts 1100, 1102 are shown with their corresponding conduction velocity vectors in a different greyscale on a CV map 1104.

According to another aspect of the disclosure, the cardiac activation wavefront is displayed by sequentially displaying conduction velocity vectors according to their local activation times and local conduction velocities, starting with the source node identified in block 806 and proceeding along the path identified in block 808.

In some embodiments, the cardiac activation wavefront can be displayed with animation (e.g., over the mean cycle length of the cardiac activation), such as by removing or dimming prior conduction velocity vectors as subsequent conduction velocity vectors appear (making it appear as if the conduction velocity vector is moving across the graphical representation of the cardiac geometry). For example, each conduction velocity vector can initially illuminate according to its local activation time, and can stay illuminated for a time based upon its local conduction velocity.

It is also contemplated to display multiple cardiac activation wavefronts sequentially. For example, if the user identifies three seed nodes (or if system 8 is used to automatically identify three seed nodes), then three cardiac activation wavefronts can be identified, and then displayed in sequence, separated by a user-defined delay period.

It is also contemplated that these multiple wavefronts can be sorted and/or prioritized, either manually by a user or automatically according to one or more preset criteria. For example, the multiple wavefronts can be sorted and/or prioritized according to their respective average cycle lengths, their respective average conduction velocities, or the like. Once sorted and/or prioritized, the wavefronts can be displayed in sequence as described above (e.g., with a user-defined delay between the display of successively sorted wavefronts).

Those of ordinary skill in the art will also appreciate that a single cardiac activation wavefront may appear to be multiple cardiac activation wavefronts if scarring or other blockage interrupts the path of the cardiac activation wavefront. Thus, in embodiments, multiple cardiac activation wavefronts (e.g., $w_1, w_2, \ldots, w_n$) can be merged into a single cardiac activation wavefront (e.g. w') by detecting the blockage (e.g., using low voltage values and fractionated electrograms/potentials), identifying the wavefronts that should be merged, and then merging the wavefronts sequentially (e.g., $w_1+w_2 \rightarrow w'$, then $w'+w_3 \rightarrow w'$, and so forth until all n wavefronts are merged into a final w'). For example, when merging $w_1$ and $w_2$, the final node of $w_1$ can be connected to the source node of $w_2$. Set forth below is one suitable wavefront-merging algorithm:

---
Multiple Wavefronts Merge

Input: n wavefronts $w_1, w_2, \ldots, w_n$
Output: the merged wavefronts w'
1　Set w' = $w_1$
2　For every wavefront $w_i$
3　　Identify the connected region R between $w_i$ and w'.
4　　Sort $w_i$ and w' based on the wavefront direction and get the order of $w_i$ and w'
5　　w' ← Combine $w_i$, R, w'.
6　　Reassign the activation time based on the order of $w_i$ and w'
---

Although several embodiments of this invention have been described above with a certain degree of particularity, those skilled in the art could make numerous alterations to the disclosed embodiments without departing from the spirit or scope of this invention.

For example, although aspects of the disclosure relate to the use of EP data to map cardiac activation wavefronts, it is contemplated that non-EP data can also be used to map cardiac activation wavefronts. Suitable non-EP data includes, without limitation, ultrasound-based metrics, MRI based functional images, contact catheter-based cardiac motion measurements, and other data that provide information about the direction and speed of different anatomical locations in the heart chamber (e.g., cardiac mechanics, cardiac fluid dynamics, and any other physical phenomena representable in a three dimensional field). The ordinarily skilled artisan will appreciate how to adapt and extend the teachings herein to such non-EP data.

As another example, multiple catheters can be used to collect EP data that can be leveraged according to the teachings herein.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:
1. A method of mapping a cardiac activation wavefront, comprising:
receiving a geometry of at least a portion of a cardiac surface, the geometry comprising a plurality of nodes;
receiving electrophysiology data for the portion of the cardiac surface, the electrophysiology data comprising conduction velocity data;
assigning a conduction velocity vector to each node of the plurality of nodes using the conduction velocity data, thereby creating a plurality of conduction velocity vectors;
defining a plurality of directed edges connecting the plurality of nodes, thereby creating a directed conduction velocity graph;
assigning a weight to each directed edge of the plurality of directed edges in the directed conduction velocity graph, thereby creating a weighted directed conduction velocity graph; and
identifying a cardiac activation wavefront using the weighted directed conduction velocity graph.

2. The method according to claim 1, wherein assigning a conduction velocity vector to each node of the plurality of nodes using the conduction velocity data comprises interpolating the conduction velocity data to assign each conduction velocity vector to an associated node of the plurality of nodes.

3. The method according to claim 1, wherein defining a plurality of directed edges connecting the plurality of nodes comprises repeating, a plurality of times:
selecting a first node within the plurality of nodes, the first node having assigned thereto a first conduction velocity vector;
selecting a second node within the plurality of nodes, the second node having assigned thereto a second conduction velocity vector;
defining a first vector connecting the first node to the second node;
defining a second vector connecting the second node to the first node;
computing a first angle between the first conduction velocity vector and the first vector;
computing a second angle between the second conduction velocity vector and the second vector;
defining a directed edge from the first node to the second node when the first angle is less than 90 degrees; and
defining a directed edge from the second node to the first node when the second angle is less than 90 degrees.

4. The method according to claim 1, wherein assigning a weight to each directed edge of the plurality of directed edges in the directed conduction velocity graph comprises, for each directed edge, assigning a weight based upon a first conduction velocity vector assigned to a first node of the respective directed edge and a second conduction velocity vector assigned to a second node of the respective directed edge.

5. The method according to claim 1, wherein assigning a weight to each directed edge of the plurality of directed edges in the directed conduction velocity graph comprises, for each directed edge, assigning a weight based upon a time required to travel between a first node of the respective directed edge and a second node of the respective directed edge.

6. The method according to claim 1, wherein assigning a weight to each directed edge of the plurality of directed edges in the directed conduction velocity graph comprises, for each directed edge, assigning a weight based upon a first peak-to-peak voltage at a first node of the respective directed edge and a second peak-to-peak voltage at a second node of the respective directed edge.

7. The method according to claim 1, wherein assigning a weight to each directed edge of the plurality of directed edges in the directed conduction velocity graph comprises, for each directed edge, assigning a weight based upon a first cycle length at a first node of the respective directed edge and a second cycle length at a second node of the respective directed edge.

8. The method according to claim 1, wherein assigning a weight to each directed edge of the plurality of directed edges in the directed conduction velocity graph comprises, for each directed edge, assigning a weight based upon a first direction of a first conduction velocity vector assigned to a first node of the respective directed edge and a second direction of a second conduction velocity vector assigned to a second node of the respective directed edge.

9. The method according to claim 1, wherein assigning a weight to each directed edge of the plurality of directed edges in the directed conduction velocity graph comprises, for each directed edge, assigning a weight based upon one or more of conduction velocity consistency, conduction velocity regularity, electrogram morphological similarity, and contact force.

10. The method according to claim 1, wherein identifying a cardiac activation wavefront using the weighted directed conduction velocity graph comprises:
    identifying a subset of the plurality of nodes, through which the cardiac activation wavefront passes;
    identifying a source node within the subset of the plurality of nodes; and
    identifying a path of the cardiac activation wavefront, starting with the source node, through the subset of the plurality of nodes.

11. The method according to claim 10, wherein identifying a subset of the plurality of nodes comprises:
    selecting a seed node within the plurality of nodes;
    adding the seed node to the subset of the plurality of nodes; and
    applying a growing algorithm starting from the seed node to add one or more additional nodes to the subset of the plurality of nodes,
    wherein the growing algorithm:
        computes a similarity measurement between a first node within the subset of the plurality of nodes and a second node, adjacent the first node and outside of the subset of the plurality of nodes, and
        adds the second node to the subset of the plurality of nodes when the similarity measurement satisfies a similarity criterion.

12. The method according to claim 11, wherein the similarity measurement is based, at least in part, upon a direction of a conduction velocity vector assigned to the first node and a direction of a conduction velocity vector assigned to the second node.

13. The method according to claim 10, wherein identifying a source node within the subset of the plurality of nodes comprises applying a strongly connected components analysis to the subset of the plurality of nodes.

14. The method according to claim 10, wherein identifying a path of the cardiac activation wavefront, starting with the source node, through the subset of the plurality of nodes comprises identifying a lowest-cost path, starting with the source node, through the subset of the plurality of nodes.

15. The method according to claim 1, further comprising:
    displaying a graphical representation of the geometry; and
    displaying a graphical representation of the cardiac activation wavefront on the graphical representation of the geometry.

16. The method according to claim 15, wherein displaying a graphical representation of the cardiac activation wavefront on the graphical representation of the geometry comprises animating the graphical representation of the cardiac activation wavefront on the graphical representation of the geometry.

17. The method according to claim 16, wherein animating the graphical representation of the cardiac activation wavefront on the graphical representation of the geometry comprises animating the graphical representation of the cardiac activation wavefront over a time duration based upon a mean cardiac cycle length.

18. The method according to claim 1, wherein identifying a cardiac activation wavefront using the weighted directed conduction velocity graph comprises:
    identifying a first cardiac activation wavefront using the weighted directed conduction velocity graph; and
    identifying a second cardiac activation wavefront using the weighted directed conduction velocity graph, and wherein the method further comprises:
        displaying a graphical representation of the geometry;
        displaying a graphical representation of the first cardiac activation wavefront on the graphical representation of the geometry; and
        displaying a graphical representation of the second cardiac activation wavefront on the graphical representation of the geometry after preset delay time has elapsed following displaying the graphical representation of the first cardiac activation wavefront.

19. The method according to claim 1, wherein identifying a cardiac activation wavefront using the weighted directed conduction velocity graph comprises:
    identifying a first cardiac activation wavefront using the weighted directed conduction velocity graph; and
    identifying a second cardiac activation wavefront using the weighted directed conduction velocity graph, and wherein the method further comprises:
        determining that the first cardiac activation wavefront and the second cardiac activation wavefront should be merged;
        merging the first cardiac activation wavefront and the second cardiac activation wavefront into a merged cardiac activation wavefront;
        displaying a graphical representation of the geometry; and displaying a graphical representation of the merged cardiac activation wavefront;
on the graphical representation of the geometry.

20. The method according to claim 1, wherein identifying a cardiac activation wavefront using the weighted directed conduction velocity graph comprises:
   identifying a source of the cardiac activation wavefront using the weighted directed conduction velocity graph; and
   identifying a path of the cardiac activation wavefront through the weighted directed conduction velocity graph.

21. A method of mapping cardiac activation wavefronts, comprising:
   establishing a mesh comprising a plurality of mesh nodes;
   assigning each mesh node of the plurality of mesh nodes a conduction velocity vector;
   defining a plurality of weighted directed edges interconnecting the plurality of mesh nodes, thereby creating a weighted directed conduction velocity graph;
   identifying at least one cardiac activation wavefront using the weighted directed conduction velocity graph; and
   displaying the identified at least one cardiac activation wavefront on a graphical representation of a cardiac geometry.

22. A system for mapping cardiac activation wavefronts, comprising:
   a cardiac activation wavefront identification processor configured:
      to receive as input a mesh comprising a plurality of mesh nodes and electrophysiology data comprising conduction velocity data;
      to assign a conduction velocity vector to each mesh node of the plurality of mesh nodes using the conduction velocity data;
      to define a plurality of weighted directed edges interconnecting the plurality of mesh nodes, thereby creating a weighted directed conduction velocity graph; and
      to identify at least one cardiac activation wavefront using the weighted directed conduction velocity graph; and
   a mapping processor configured to display the identified at least one cardiac activation wavefront on a graphical representation of a cardiac geometry.

* * * * *